United States Patent [19]

Wand et al.

[11] Patent Number: 5,585,036
[45] Date of Patent: Dec. 17, 1996

[54] LIQUID CRYSTAL COMPOUNDS CONTAINING CHIRAL 2-HALO-2-METHYL ETHER AND ESTER TAILS

[75] Inventors: Michael D. Wand, Boulder; Kundalika M. More, Denver; William N. Thurmes, Longmont, all of Colo.

[73] Assignee: Displaytech, Inc., Boulder, Colo.

[21] Appl. No.: 461,377

[22] Filed: Jun. 5, 1995

Related U.S. Application Data

[63] Continuation-in-part of Ser. No. 193,254, Feb. 8, 1994, Pat. No. 5,453,218, which is a continuation-in-part of Ser. No. 6,263, Jan. 19, 1993, Pat. No. 5,422,037, which is a continuation-in-part of Ser. No. 164,233, Mar. 4, 1988, Pat. No. 5,051,506.

[51] Int. Cl.$^6$ .......................... C09K 19/52; C09K 19/34; C07D 239/02; C07C 43/00

[52] U.S. Cl. ..................... 252/299.01; 252/299.61; 252/299.63; 252/299.66; 252/299.67; 252/299.64; 504/242; 504/336; 504/346; 548/136; 568/588; 568/647; 570/123; 570/127

[58] Field of Search .............. 252/299.01, 299.61, 252/299.63, 299.64, 299.65, 299.66, 299.67; 544/242, 336, 346; 548/136; 568/588, 647; 570/123, 127

[56] References Cited

U.S. PATENT DOCUMENTS

| | | | |
|---|---|---|---|
| 4,556,727 | 12/1985 | Walba | 252/299.01 |
| 4,592,858 | 6/1986 | Higuchi | 252/299.66 |
| 4,695,650 | 9/1987 | Walba et al. | 252/299.67 |
| 4,695,651 | 9/1987 | Higuchi | 252/299.01 |
| 4,725,688 | 2/1988 | Taguchi et al. | 252/299.61 |
| 4,728,458 | 3/1988 | Higuchi et al. | 252/299.65 |
| 4,798,680 | 1/1989 | Nohira et al. | 252/299.01 |
| 4,831,182 | 5/1989 | Higuchi | 252/299.66 |
| 4,835,295 | 5/1989 | Walba et al. | 252/299.61 |
| 4,886,619 | 12/1989 | Janulis | 252/299.01 |
| 4,954,600 | 9/1990 | Hachiya | 252/299.01 |
| 5,051,506 | 9/1991 | Wand et al. | 252/299.01 |
| 5,130,048 | 7/1992 | Wand et al. | 252/299.01 |
| 5,167,855 | 12/1992 | Wand et al. | 252/299.01 |
| 5,180,520 | 1/1993 | Wand et al. | 252/299.01 |
| 5,254,747 | 10/1993 | Janulis | 252/299.01 |
| 5,389,291 | 2/1995 | Reiffenrath et al. | 252/299.61 |
| 5,399,291 | 3/1995 | Janulis et al. | 252/299.01 |
| 5,422,037 | 6/1995 | Wand et al. | 252/299.61 |
| 5,437,812 | 8/1995 | Janulis et al. | 252/299.01 |
| 5,453,218 | 9/1995 | Wand et al. | 252/299.01 |

FOREIGN PATENT DOCUMENTS

| | | |
|---|---|---|
| 0255236 | 2/1988 | European Pat. Off. . |
| 0267585 | 5/1988 | European Pat. Off. . |
| 0278665 | 8/1988 | European Pat. Off. . |
| 62-111939 | 5/1987 | Japan . |
| 86/06373 | 11/1986 | WIPO . |
| 87/05018 | 8/1987 | WIPO . |

OTHER PUBLICATIONS

Walba et al. (1986) J. Amer. Chem. Soc. 108:5210–5221.
Walba et al. (1986) J. Amer. Chem. Soc. 108:7424–7425.
Wand et al. (1991) Ferroelectrics 121:219–223.

*Primary Examiner*—Shean C. Wu
*Attorney, Agent, or Firm*—Greenlee, Winner and Sullivan, P.C.

[57] ABSTRACT

This invention provides chiral nonracemic compounds of general formula I which are useful as components of FLC compositions in SSFLC and DHFLC devices:

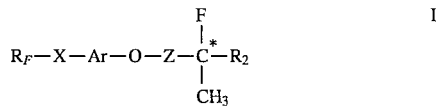

wherein Z is a C=O group or a $CH_2$ group, $R_F$ is a partially or fully fluorinated alkyl or alkenyl group, $R_2$ is selected from an alkyl, alkenyl or alkynyl group in which one or more $CH_2$ groups can optionally be substituted with one or two halogen atoms or in which one or more non-neighboring $CH_2$ can be replaced with an O, S or an alkyl silyl group, $S_i(R_A)(R_B)$, in which $R_A$ and $R_B$, independently of one another, are small alkyl or alkenyl groups having from one to six carbon atoms, * indicates the chiral carbon and where Ar can be a one, two, or three aromatic ring LC core moieties. In particular, the core can have one to three, aromatic rings which are optionally linked by linking groups including O, S, $CH_2S$, $SCH_2$, $CH_2CH_2$, $CH_2O$, $OCH_2$, $CH_2CO_2$, $CH_2OCO$, COO, OOC, COS, a double or a triple bond and can contain cyclohexyl cyclohexenyl rings which are optionally substituted or which contain O atoms in the ring.

22 Claims, No Drawings

LIQUID CRYSTAL COMPOUNDS CONTAINING CHIRAL 2-HALO-2-METHYL ETHER AND ESTER TAILS

REFERENCE TO RELATED APPLICATIONS

This application is a continuation-in-part of Ser. No. 193,254, now U.S. Pat. No. 5,455,218, filed Feb. 8, 1994 which in turn was a continuation-in-part of Ser. No. 006,263, now U.S. Pat. No. 5,422,037, filed Jan. 19, 1993, which in turn is a continuation-in-part of Ser. No. 164,235, filed Mar. 4, 1988, now U.S. Pat. No. 5,051,506, issued Sep. 29, 1991. U.S. Pat. Nos. 5,453,218 and 5,422,037 and U.S. Pat. No. 5,051,506 are incorporated by reference herein in their entirety.

FIELD OF THE INVENTION

The present invention relates to compounds and liquid crystal compositions containing them which are useful in electro-optical and display device applications.

BACKGROUND OF THE INVENTION

Lagerwall and Clark described the surface-stabilized ferroelectric liquid crystal (SSFLC) effect and its application to electro-optic shutters and display devices (U.S. Pat. Nos. 4,367,924 and 4,563,059). SSFLC devices can display electro-optic effects with very fast (sub-microsecond) switching speeds.

Tilted smectic liquid crystal phases particularly smectic C phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Lee Ulis, Fr) 36:L-69). The ferroelectric polarization density is an intrinsic property of the material making up the phase and has a magnitude and sign for a given material under a given set of conditions.

In SSFLC cells, the FLC is aligned between transparent electrodes in the so-called "bookshelf" alignment in which the smectic layers are substantially perpendicular to the electrodes and the long axis of the FLC molecules are parallel to the electrodes. In this configuration, the natural helix typically formed in the ferroelectric phase is suppressed by surface interactions in the cell. Suppression of the helix results in a bistable cell in which the optic axis of the cell can be rotated in the plane of the electrodes by 2θ, where θ is the tilt angle, by changing the sign of the applied driving voltage. Tilt angle is an intrinsic property of a FLC material. This switching of rotation of the optic axis can be employed for light modulation. Within a large range of electric field strengths, the switching speed (optical rise time) is inversely proportional to applied field strength and polarization or dipole density ($P_s$), and directly proportional to orientational viscosity. Fast switching speeds are associated with FLC phases which possess high polarization density and low orientational viscosity.

In order to suppress the helix, the SSFLC cell thickness (d) must be comparable to or smaller than the magnitude of the pitch of the helix in the ferroelectric phase. Thus, for applications in the visible in which cell thicknesses of 0.5–6 μm are most useful (assuming a birefringence of 0.15–0.3), the SSFLC natural ferroelectric phase helix pitch in the FLC should be longer than 0.5–10 μm.

Electro-optic effects in the FLC cells in which the helix in the smectic C* phase is not suppressed by surface-stabilization have also been described. The distorted helix ferroelectric (DHF) effect, described for example in Ostovski et al., Advances in Liquid Crystal Research and Applications, Oxford/Budapest. (1980) page 469 and in Funfschilling and Schadt (1989) J. Appl. Phys. 66(8):3877–3882), is observed in FLCs aligned between electrode plates in which the natural helix pitch in the smectic C* (or other chiral tilted smectic ferroelectric) phase is sufficiently tight, i.e., shorter than the FLC cell thickness (d), so that the helix is not suppressed. DHFLC electro-optic devices have an FLC aligned between electrode plates. Most typically the FLC is planar aligned and in the "bookshelf" geometry. A driving voltage is applied to the electrodes to generate an electric field across the FLC layer. Unlike, SSFLC devices, the natural helix of the aligned chiral smectic phase is present in the aligned FLC material in the DHF device. The helix forms parallel to the plates and perpendicular to the smectic layers. The magnitude of the pitch of the helix is the distance along the helix axis for one full turn of the helix and the sign of the pitch (+ or –) represents the direction of twist of the helix. The term "tight" pitch, which can be a positive or negative value, is associated with shorter axial lengths for one full turn of the helix. The term "pitch" as used herein refers to the magnitude of the pitch; the terms "sign of the pitch" or "twist" refer to the direction of twist of the helix.

When the magnitude of the ferroelectric C* phase, helical pitch is comparable to the wavelength of visible light, a striped pattern appears in the device and in effect a diffraction grating is formed. If the magnitude of the pitch is less than the wavelength of light (and preferably less than ½λ of light), light diffraction is minimized and the apparent refractive index of the FLC is the average over many director orientation of the helix. In the field-free state with zero applied electric field and with no surface stabilization, the C* helix is in its natural state. The molecular director, ñ, makes an angle, θ, with the layer normal. In the field-free (E=0) state, due to the presence of the helix, averaging occurs and the apparent optic axis of the DHFLC coincides with the helix axis.

If the voltage applied across the FLC layer is above a certain critical level $E_c$, the helix is completely unwound forming two distinct optical states, as in an SSFLC device. Application of a voltage below $E_c$ deforms the helix, generating an effective rotation of the optic axis of the DHFLC. The orientation of the optic axis of the DHFLC layer can be changed in a continuous fashion proportional to the applied electric field changing the optical anisotropy of the FLC. DHF cells display rotation of their optic axis that is dependent on the magnitude of the applied electric field and also exhibit a change in apparent birefringence (Δn) as a function of the magnitude of the applied electric field.

The maximum field-induced angle of rotation of the optic axis of the DHFLC is θ, the tilt angle of the material. A maximum field induced optic axis rotation of 2θ can be obtained by application of a +/– voltage step, +/– $E_{max}$, where $E_{max}$ is the minimum voltage required to obtain a rotation of θ and the magnitude of $E_{max}$ is less than $E_c$.

DHF-effect cells typically exhibit significantly lower apparent refractive index than SSFLC cells due to the averaging noted above. Thus, for a given desired optical retardation, DHF cells are typically thicker than comparable SSFLC cells. Birefringence for DHFLC cells typically ranges from about 0.06 to 0.13, about ½ that of SSFLC cells. DHFLC waveplates are as a consequence, typically, thicker than comparable SSFLC waveplates. High birefringence materials are thus useful in DHF application to minimize cell thicknesses.

$E_c$ is inversely proportional to the spontaneous polarization of the FLC and the ferroelectric phase pitch, having the relationship:

$$E_c P_s \propto \left(\frac{1}{p^2}\right)$$

Thus, the higher the spontaneous polarization and longer the pitch, the lower the voltage necessary to control the effect. Response time ($\tau$) for the DHFLC cell is a function of pitch, tilt angle and viscosity:

$$\tau \propto \gamma \frac{p^2}{\theta^2}$$

where $\gamma$ is the orientational viscosity and $\theta$ is the tilt angle. Increasing $P_S$ lowers the threshold voltage, but does not increase the speed, while tightening the pitch increases both the speed and $E_c$. By increasing both $P_S$ and decreasing p, the response speed can be significantly increased while maintaining a low threshold voltage. Also decreasing the viscosity improves the response time.

Contrast ratio of a device is defined as the ratio of the transmitted light in an ON (maximal white light transmitted through the device) and an OFF (minimal white light transmitted through the device) state. Maximum contrast is obtained when the voltage step applied across the cell rotates the optic axis by a total of 45° between OFF and ON states. Maximum transmission in the ON state can be limited if the total optic axis rotation is less than 45°, as in FLC's which have tilt angles less than 22.5°. Most often, however, contrast is limited by light leaking through in the OFF state, a function of the quality of cell alignment. Minimal OFF state transmission in both SSFLC and DHFLC requires good uniform alignment.

It is well-known in the art that improved alignment and contrast ratio in SSFLC cells can be facilitated by an FLC having a long pitch N* phase at higher temperatures to the ferroelectric tilted chiral smectic phase (see for example WO 87/06021). To facilitate alignment in SSFLCs, N* pitch should be at least equal to d, and preferably 4d or more. It is also well-known in the art for the preparation of SSFLC cells that cell alignment is further facilitated by the presence in the FLC of a smectic A phase intermediate in temperature between the chiral tilted smectic ferroelectric phase and the N* phase. SSFLC cells, as noted above, however, are also considered in the art to require relatively long pitch (typically longer than d and preferably longer than 4d) in their ferroelectric phase.

Methods analogous to those that had been successful in improving the alignment and contrast of SSFLC cells can be employed to improve the alignment and contrast in DHFLC cells. Wand et al. U.S. Ser. No. 832,414, filed Feb. 7, 1992, which is incorporated in its entirety herein by reference, reports that compositions having a tight pitch ferroelectric phase, e.g., a smectic C* phase, and a long pitch N* phase at higher temperatures can be aligned using methods such as those described in WO 87/06021. These methods combine cell surface treatment (i.e., alignment layers) with cooling of the FLC in contact with the treated surfaces of the cell plates from the nematic phase to the ferroelectric phase. Good FLC alignment and high DHFLC cell contrast result. It was also found by Wand et al. U.S. Ser. No. 832,414 that the presence of an orthogonal smectic phase, such as a smectic A phase, intermediate in temperature between the nematic and the ferroelectric phases further facilitates good alignment and the generation of high contrast DHFLC cells.

A basic requirement for application of ferroelectric liquid crystals in electro-optical devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases. The components of FLC mixtures can also be adjusted to vary N* pitch and C* pitch.

Thermotropic liquid crystal molecules typically possess structures which combine generally linear and generally rigid liquid crystal core coupled with two relatively "floppy" tails (see Demus et al.) (1974) Flussige Kristalle In Tabellen, VEB Deutscher Verlag fur Grundstoffindustrie, Lebzig for a compilation of the molecular structures of LC molecules). FLC dopants typically possess rigid LC cores and at least one flexible tail. FLC materials have been prepared by the introduction of a stereocenter into one (or both) of the tails, thus introducing chirality.

In bistable SSFLC applications, large $P_S$ (spontaneous polarization density), fast rise time, low orientational viscosity, long N* pitch and long C* pitch are desirable. Large $P_S$, fast rise time, and low orientational viscosity all relate to the switching speed upon application of an optimal field. The N* and C* pitch are both manifestations of the chirality of the liquid crystal material and are intrinsic properties of FLC components. Although both are helices formed in the liquid crystal, they propagate in different directions and bring different complications to a FLC light modulator. The N* helix, in a surface stabilized FLC with planar geometry, runs perpendicular to the substrates, whereas in the same FLC, the C* helix runs parallel to the substrate. As noted above, the N* helical repeat length or pitch, measured at the N→A or N→C transition, should be more than four times the width of the cell to give preferred consistent alignment of the FLC (Uchida, T. et al. (1989) Liquid Crystals 5:1127).

In DHFLC applications large $P_S$, fast rise time, low orientational viscosity also are desirable and a very tight C* pitch is required. For good alignment, DHFLC materials preferably combine long N* pitch with the very tight C* pitch.

SUMMARY OF THE INVENTION

The present invention provides new classes of FLC compounds which impart improved properties of LC and FLC compositions. The compounds of this invention have 2-fluoro-2-methyl alkoxyl or 2-fluoro and 2-fluoro-2-methyl ester chiral tails and partially or fully fluorinated achiral tails. The compounds of the present invention have general formula I:

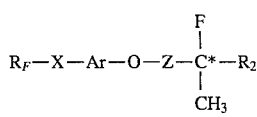

$$R_F—X—Ar—O—Z—\overset{\overset{F}{|}}{\underset{\underset{CH_3}{|}}{C^*}}—R_2 \quad \text{I}$$

where Z is C=O group or a $CH_2$ group, $R_F$ is a partially or fully fluorinated alkyl or alkene group, $R_2$ is selected from an alkyl, alkenyl or alkynyl group in which one or more $CH_2$ groups can optionally be substituted with one or two halogen atoms or in which one or more non-neighboring $CH_2$ can be replaced with an O, S or an alkyl silyl group, $S_1(R_A)(R_B)$, in which $R_A$ and $R_B$, independently of one another, are small alkyl or alkene groups having from one to six carbon atoms, * indicates the chiral carbon and where Ar can be a one, two, or three aromatic ring LC core moieties but, in particular, can be those cores having one, two or three aromatic rings of the general formula:

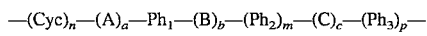

$$—(Cyc)_n—(A)_a—Ph_1—(B)_b—(Ph_2)_m—(C)_c—(Ph_3)_p—$$

where n, m, and p, independently of one another, are 0 or 1; a, b and c are either 0 or 1 and a+b+c is 2, 1 or 0; A, B and C, independently of one another, are selected from the group of O, S, $CH_2S$, $SCH_2$, $CH_2CH_2$, $CH_2O$, $OCH_2$, $CH_2CO_2$, $CH_2OCO$, COO, OOC, COS, a double or triple bond; Cyc is a 1,4-cyclohexyl ring or a 1,4-cyclohexenyl ring, either of which can be further substituted with halogen atoms or cyano groups and wherein one or two non-neighboring $CH_2$ groups of the ring can be replaced with an O atom; the aromatic rings $Ph_1$, $Ph_2$ and $Ph_3$ independently of one another, are selected from the group 1,4-phenyl, 1,4-phenyl substituted with one or two halogen atoms, 1,4-phenyl in which one or two of the ring carbons are replaced with nitrogen atoms or a thiadiazole ring; X is an O or a single bond.

$R_F$ can be straight-chain or branched and preferably have from one to about twenty carbon atoms.

Chiral, non-racemic 2-fluoro-2-methyl alkoxy and 2-fluoro-2-methyl ester LC compounds with fluorinated alkyl or alkenyl achiral tails, particularly those LC compounds with two aromatic rings, have substantially higher polarization than analogous compounds having non-fluorinated alkyl and alkenyl achiral tails.

This invention provides LC and FLC compositions, mixtures of two or more component compounds, comprising one or more of the chiral nonracemic compounds of formula I.

In general, the chiral nonracemic compounds of this invention are useful as components of liquid crystal compositions to impart desired properties to the composition. Certain of these compounds can impart fast switching speeds to low polarization materials to form FLC useful for SSFLC or DHFLC applications. Certain of these compounds can affect the N* and/or C* pitch of FLC compositions. Certain of these compounds, for example those having N* pitch which is opposite in sign from their polarization density, can be employed to elongate N* pitch without detriment to polarization density, i.e. can function as pitch compensation agents. Certain of the compounds having N* pitch opposite in sign to C* pitch are particularly useful to obtain mixtures having short C* pitch essential for DHFLC operation in combination with long N* pitch preferred for better FLC layer alignment and improved contrast in liquid crystal devices.

DETAILED DESCRIPTION OF THE INVENTION

The chiral nonracemic 2-fluoro-2-methyl alkoxy compounds:

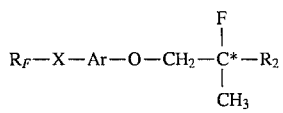

$$R_F—X—Ar—O—CH_2—\overset{\overset{F}{|}}{\underset{\underset{CH_3}{|}}{C^*}}—R_2 \quad \text{II}$$

or the 2-fluoro-2-methyl ester compounds:

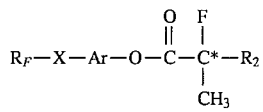

$$R_F—X—Ar—O—\overset{\overset{O}{\|}}{C}—\overset{\overset{F}{|}}{\underset{\underset{CH_3}{|}}{C^*}}—R_2 \quad \text{III}$$

of this invention containing a wide variety of cores Ar to provide useful components of LC or FLC compositions, where Ar is:

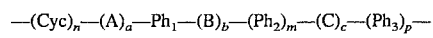

$$—(Cyc)_n—(A)_a—Ph_1—(B)_b—(Ph_2)_m—(C)_c—(Ph_3)_p—$$

The chiral tail groups, generically designated R* in Tables 1–6 of exemplary cores, can have either the S or R configuration.

In general, suitable liquid crystal cores are rigid, linear moieties. Preferred cores are those that are chemically stable and which do not impart high orientational viscosity in the liquid crystal phase. Specific cores of this invention have one, two or three aromatic rings and optionally contain a cyclohexane or cyclohexene ring.

The cyclohexane or cyclohexene ring of the core is preferably linked at its 1 and 4 positions between $R_FX$ and $—(A)_a—Ph_1$. The cyclohexane or cyclohexene rings may be further substituted with halogen atoms or cyano groups and one or two non-neighboring $CH_2$ groups of the ring may be substituted with an O atom. The cyclohexane or cyclohexene ring can be directly linked to an aromatic ring of the core or linked through a linking group, for example a, $CH_2CH_2$, $CH_2O$, $OCH_2$, $CO_2$ or OOC group. The preferred linking groups are $CH_2CH_2$, $CH_2O$, and $OCH_2$. The cyclohexane or cyclohexene ring is preferably in the trans configuration. The double bond of the cyclohexene ring is preferably in the 3,4-bond adjacent to the site of $R_FX$ group substitution. The preferred cyano substitution is at the axial 1 position on the ring carbon bonded to the $R_FX$ group:

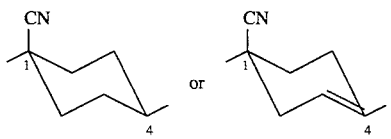

The preferred oxygen-containing cyclohexane ring is that with oxygens in placed of the 3 and 5 carbons as indicated:

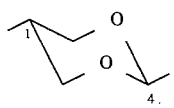

The aromatic rings of the core $Ph_1$, $Ph_2$ and $Ph_3$ can in general be any aromatic ring, but more specifically are selected from the group 1,4-phenyl, 1,4-phenyl substituted with one or two halogens, 1,4-phenyl in which one or two ring carbons are replaced with nitrogen atoms. Nitrogen-containing aromatic $Ph_{1-3}$ include among others pyrimidinyl, pyridinyl, diazinyl, pyrazinyl and pyridizinyl rings. Preferred halogens are fluorine.

Exemplary Ph$_{1-3}$ include, but are not limited to, 1,4-substituted phenyl rings: mono- and dihalogenated rings:

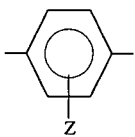

mono- and difluoro rings, including ortho, meta and ortho, meta fluorine substitution:

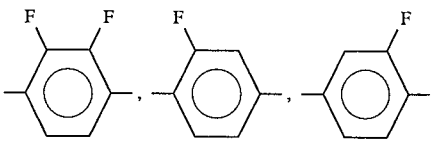

2,5-substituted pyridine rings:

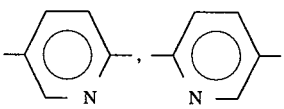

2,5-substituted pyrimidine rings:

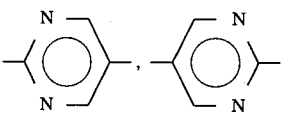

2,5-substituted pyrazine rings:

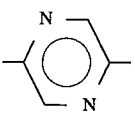

3,6-substituted pyridizine rings:

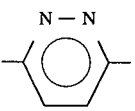

and thiadiazole rings:

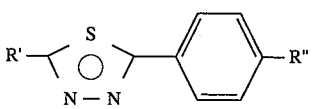

Preferred nitrogen-containing Ph$_{1-3}$ moieties are 2,5-substituted pyridine and 2,5-substituted pyrimidine rings.

Aromatic rings of the core can be directly linked to one another, preferably in a para arrangement, or by means of linking groups B and C. Compounds of this invention can optionally have one or two linking groups. When present, preferred linking groups are a triple bond or COO and OOC groups. Again the Ph$_{1-3}$ and the linking groups are preferably linked in a para arrangement to generate a generally linear core.

Compounds of this invention having two aromatic rings in the core includes those of formulas Ia and Ib where the chiral nonracemic 2-fluoro-2-methyl alkoxy and the 2-fluor-methyl ester tails are indicated as R*:

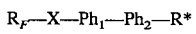 Ia/Ia'

 Ib/Ib'

R$_F$, X, Ph$_1$, Ph$_2$ and B are as defined above for formula I. Formulas Ia' and Ib' represent those formulas where the indicated core is reversed with respect to R, X and R*. Tables 1 and 2 provide examples of the cores of Ia and Ib respectively. Compounds of formula Ia where at least one of Ph$_1$ or Ph$_2$ is a 2,5-pyridinyl or a 2,5-pyrimidyl are of particular interesting. Compounds of formula Ia include phenylbenzoates, phneylpyridines, phenylpyrimidines and their halogenated analogs. Compounds of formula Ib include phenylbenzoates, reverse phenylbenzoates and tolanes, among other. Tolanes, where B is a triple bond, are of particular interest for applications requiring high birefringence. Thiadiazole rings are preferably linked to a 1,4-phenyl ring.

Compounds of this invention having three aromatic rings includes those of formulas Ic–If:

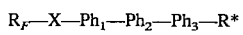 Ic/Ic'

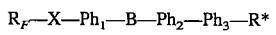 Id

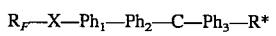 Ie

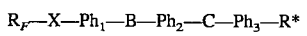 If/If' where R$_F$, X, Ph$_{1-3}$, B and C are as defined above for formula I. Formulas Ic' and If' represent those formulas where the core is reversed with respect to R$_F$—X and R*. Compounds of formula Ic where at least one of Ph$_{1-3}$ is a 2,5-pyridinyl or 2,5-pyrimidinyl ring are of interest. Compounds of formula Ic where one of Ph$_{1-3}$ is a 2,5-pyrimidinyl are of particular interest in applications requiring FLC components having N* pitch and polarization of opposite signs. Compounds of formula Id and Ie include phenyltolanes, where B or C is a triple bond; biphenylbenzoates, where B or C is COO; phenyl (phenylbenzoates), where B or C is OOC. Phenyltolanes of formula Id and Ie are further useful in high birefringence applications. Compounds of formula If include those in which both B and C are triple bonds and in which one of B or C is COO or OOC and the other of B or C is a triple bond. Compounds of formula If having at least one triple bond are further useful in high birefringence applications. Exemplary cores of formulas Ic–If are given in Tables 3–5. Table 4 exemplifies cores of both formulas Id and Ie dependent upon the orientation of the core with respect to R$_F$—X and R*. Compounds of this invention having a cyclohexene or cyclohexane ring includes those of formulas Ig and Ih:

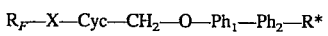 Ig

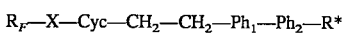 Ih where R$_F$, X, Cyc, Ph$_{1-2}$ are as defined for formula I above. Cyc includes both a trans-cyclohexyl (c-C$_6$H$_{10}$) or a trans-cyclohexenyl (c-C$_6$H$_8$), among others. In particular, Cyc can be

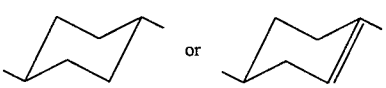

Cyc also includes cyclohexane and cyclohexene rings substituted with halogens or cyano groups. Axial substitution is preferred. Compounds of formulas Ig and Ih with a cyclohexyl group having a cyano (CN) group at the axial orientation at position 1 (i.e. where the ring is linked to $R_F$—X): cyano are further useful in applications needing negative dielectric anisotropy. Compounds of formula Ih having the oxygen containing six membered ring:

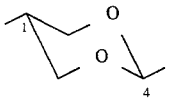

are also particularly useful in LC and FLC applications.

Compounds of formula Ig in which one of $Ph_1$ or $Ph_2$ is a 2,5-pyrimidinyl or a 2,5-pyridinyl are of interest for LC and FLC applications. Those compounds in which one of $Ph_1$ or $Ph_2$ is a 2,5-pyrimidinyl are of particular interest for such applications. Table 6 provides exemplary cores of formulas Ig and Ih.

In addition to LC cores containing two and three aromatic rings that have been detailed above, the 2-fluoro-2 methyl tails of this invention can be combined with LC cores containing one aromatic ring or those containing more than three aromatic rings. Useful core size is generally limited by mixing properties and increasing viscosity as the number of rings increases. In particular, the combination of the 2-fluoro-2-methyl chiral non-racemic tails with partially or fully fluorinated tails with LC cores having a single aromatic ring, e.g., a pyrimidine or pyridine ring, results in useful components for LC and FLC compositions. Single aromatic ring compounds of this invention include:

where $Ph_1$ is a 1,4-phenyl, a 1,4-phenyl substituted with one or two halogens, preferably fluorines, or a 1,4-phenyl in which one of two ring carbons are replaced with nitrogens. Exemplary cores of compound of formula Ii include:

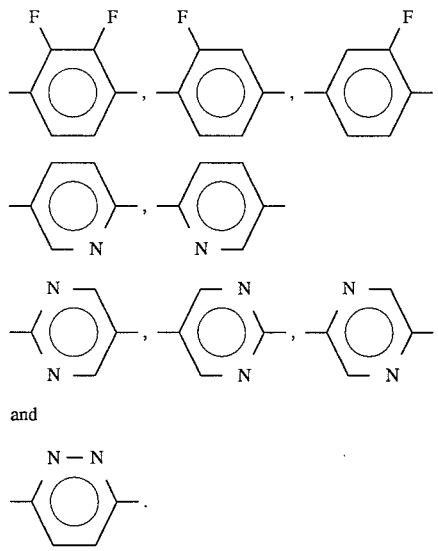

and

Further, LC cores having only cyclohexane or cyclohexene rings or derivatives thereof, can also be combined with the 2-fluoro-2-methyl alkoxy or ester tails of this invention and partial or fully fluorinated achiral tails $R_F$ to give FLC compounds. Cores having two or three cyclohexane or cyclohexene rings are typically the most useful. Dopants having cores containing only cyclohexane or cyclohexene rings tend to depress the A→C* phase transition which may be undesirable for a particular SSFLC or DHF application. However, such materials can be useful in electroclinic application or if a room temperature C* phase is present, in low birefringence SSFLC and DHF applications.

The tail units $R_F$X and R*, i.e., the chiral nonracemic O—Z—CF(CH₃)R₂ group, are preferably linked on opposite ends of the core in a para arrangement.

The compounds of the present invention have $R_F$ which can be chiral nonracemic or achiral. $R_F$ tails are partially or fully fluorinated straight-chain or branched alkyl or alkenyl groups preferably having from about three to about twenty carbon atoms. $R_F$ tails can contain cycloalkyl portions, e.g. cyclopropane moieties. Preferred alkyl tails have from about five to twelve carbon atoms. Preferred alkenyl tails have a single double bond and any double bonds may be cis or trans. Table 7 provides a list of exemplary formula of $R_F$—X—.

$R_2$ can be branched or straight-chain or contain a cycloalkyl portion, such as a cyclopropane ring. $R_2$ can include, among others, alkyl, alkenyl, alkynyl, haloalkyl, haloalkenyl, ether, thioether, alkyl silyl or alkenyl silyl groups. The first atom in $R_2$, bonded to the chiral carbon, is preferably a carbon. Preferred $R_2$ are alkyl. Preferred alkenyl and alkynyl groups are monoalkenyl and monoalkynyl groups. Preferred alkyl silyl groups comprise dimethyl silyl groups $Si(CH_3)_2$. $R_2$ groups that are ethers or thioethers can also contain one or more double bonds. Preferred ether and thioether groups contain a single O and S, respectively. Preferred $R_2$ groups contain from one to about twenty carbon atoms; more preferred $R_2$ groups contain from about two to twelve carbon atoms. Exemplary $R_2$ groups are listed in Table 8.

The chiral nonracemic 2-fluoro-2-methyl alkoxy and 2-fluoro-2-methyl ester compounds of this invention can be synthesized employing methods described in Schemes 1 and 2 and the examples, herein, by methods well-known in the art or by routine modification and/or adaptation of these methods. U.S. patent application Ser. No. 08/193,254, filed Feb. 9, 1994 describes methods for synthesis of 2-fluoro-2-methyl alkoxy compounds which can be modified or adapted for synthesis of $R_F$ substituted analogs of this invention. Starting materials for synthesis of the compounds of this invention including compounds of formulas Ia–Ii are readily available from commercial sources or by routine synthesis.

Scheme 1 outlines the synthesis of precursor 2 for the 2-fluoro-2-methyl alkoxy tail and precursor 3 for the 2-fluoro-2-methyl ester chiral tail from epoxide 1. The tails are coupled to Ar cores are indicated in the Scheme. Schemes 1 and 2 employ chemical terminology standard in the art.

Scheme 2 outlines the synthesis of an exemplary $R_F$ precursor $C_4F_9C_4H_8OH$ (4). Other precursors $R_FOH$ of this invention are available from commercial sources or can be readily synthesized by the method of Scheme 2, routine modification and/or adaptation of that method or by other methods well-known in the art.

Scheme 2 also outlines the coupling of the $R_F$ precursor to the LC core to give either the fluoroalkoxy ($R_F$—X, where X is O) or the fluoroalkyl ($R_F$—X, where X is a single bond) tail units. The scheme provides exemplary synthesis of fluorinated tail alkyl and alkoxy phenylpyrimidines, fluorinated tail alkoxy phenylpyridines and fluorinated tail alkoxy phenylbenzoates.

In general core precursors $R_F$—Ar—OH of this invention are commercially available, can be readily synthesized employing techniques well-known in the art or can be synthesized by routine adaptation of such well-known techniques. For example, U.S. Ser. No. 006,263 provides methods for synthesis of halogenated core precursors. Methods therein can also be employed to synthesize non halogenated cores such as phenylbenzoate and reverse phenylbenzoates.

As a further example, U.S. Ser. No. 763,134 provides methods of synthesis of two and three ring cores containing pyrimidine or pyridine rings. Compounds having thiadiazole core can be synthesized by well-known methods such as those described in EP application 89105489.2 or by routine adaptation of such methods.

Precursors for tolane cores (—Ph—C≡C—Ph)—, halogenated tolane cores and tolane-like cores in which Ph is a nitrogen-containing aromatic ring, such as a pyridine, pyrimidine, pyridizine or diazine ring can be synthesized by methods now well-known in the art or by routine adaptation of such methods. Examples of synthesis of such tolane cores are given in U.S. Ser. No. 784,263 filed Oct. 29, 1991.

Cores including cyclohexyl and cyclohexenyl rings can be synthesized by methods well-known in the art or by routine adaptation of such methods. For example, methods provided in WO 87/05105, DE 3906040 and U.S. Pat. No. 5,271,864 can be employed or readily adapted to synthesize compounds of the present invention.

Cyano substituted cyclohexane or cyclohexene containing cores can be synthesized by methods well-known in the art or by routine adaptation of such methods. For example, methods in WO 86/06373 can be employed.

The LC and FLC properties of compounds having chiral, non-racemic 2-fluor-2-methyl alkoxy tails have been described in U.S. patent application Ser. No. 08/193,254, filed Feb. 9, 1994. That description generally applies to the compounds of this invention.

Hosts for the FLC compositions of this invention exhibit a tilted smectic phase, typically smectic C phase and preferably a nematic phase at higher temperatures. Hosts can be racemic (achiral) or chiral nonracemic. Chiral nonracemic host compositions will exhibit a ferroelectric smectic phase, e.g. a smectic C* phase. Preferred hosts have a smectic C phase at useful device operating temperatures, e.g. about 10° C. to about 80° C. More preferred hosts have an orthogonal smectic phase, for example a smectic A phase, intermediate in temperature between the smectic C and nematic phases. A dopant suitable for use with a particular host must mix with, i.e. be soluble in that host.

FLC mixtures of this invention will typically comprise from about 5% to about 50% by weight of one or a mixture of one or more of the chiral nonracemic compounds of formula I. Due to mixing incompatibilities and other factors well appreciated in the art, not all hosts can be combined with all FLC dopants. Selection of suitable combinations of hosts with dopants can be routinely made in view of the structures of the components and/or by routine mixing experiments.

Preferred FLC compositions for use in SSFLC applications have a suitable smectic C phase host which also exhibits a nematic phase and comprise one or more of the chiral nonracemic compounds of formula I such that the C* pitch of the mixture is equal to or greater than about d and the N* pitch of the mixture is equal to or greater than about 4d (where d is desired layer thickness) at about 2° C. above the N* transition point. More preferred SSFLC compositions exhibit N* pitch equal to or greater than about 8d at about 2° C. above the N* transition point while exhibiting C* pitch equal to or greater than about d.

Preferred FLC compositions for use in DHF applications have a suitable smectic C phase host and comprises one or more of the chiral nonracemic compounds of formula I such that the N* pitch of the mixture is equal to or greater than about 4d at about 2° C. above the N* transition point and C* pitch is equal to or less that about ⅕ d. More preferred DHFLC compositions exhibit C* pitch equal to or less than about ⅒ d while retaining N* pitch greater than about 4 d.

Those of ordinary skill in the art will appreciate that variations of the methods, techniques and procedures specifically described herein can be employed to make and use the chiral nonracemic compounds and LC and FLC compositions of this invention. Various combinations of the compounds of this invention with each and art-known LC and FLC dopants and art-known host compounds can be made to achieve useful LC and FLC compositions. All such variations and combinations are within the scope of this invention.

EXAMPLE 1

Exemplary preparation of 2-fluoro-2-methyl tail precursor 2S-fluoro-2-methylheptyl toluenesulfonate (2)

Referring to Scheme 1, 0.7 ml HF (iPr)NH and 0.36 ml water was added to a cooled (0° C.) solution of 2 R-methyl-1, 2-epoxy heptane, 1, (where R is $C_4H_9$) (645 mg) in 20 ml of ethyl ether. A balloon filled with 200 ml $SiF_4$ was attached to the reaction flask. After stirring for 2 hours, the reaction mixture was quenched with 50 ml 5% aq. KF and extracted with ethyl ether. The organic layers were washed sequentially with saturated $NaHCO_3$ and brine and thereafter dried with anhydrous $NaSO_4$. The solvent was removed in vacuo and the residue dissolved in anhydrous THF (10 ml). Toluenesulfonyl chloride (TsCl, 1.05 g, 1.1 eq.) and pyridine (0.9 ml) were then added to the THF solution. The reaction was stirred 1 hr at 0° C. then allowed to stand at −20° C. until TLC showed the reaction to be complete, i.e. about 24 hr. A small amount of water (ca. 200 μl) was then added to the reaction mixture to hydrolyze excess toluenesulfonyl chloride. The solution was stirred at room temperature for about another 2 hr and then poured into water. The resultant mixture was extracted three times with ethyl acetate. The combined organic extracts were washed with brine and dried over sodium sulfate and potassium carbonate. Solvent was removed in vacuo and the resultant product 6 was purified by flash chromatography using 15% ethyl acetate in hexanes as the eluent.

Various starting materials 1 where $R_2$ is an alkyl, alkenyl, alkynyl, ether, thioether or alkyl silyl group, are readily available from commercial sources, from synthesis using well-known methods or from routine adaptation of well-known methods.

Dialkyl silyl groups can be introduced into $R_2$ groups of the compounds of this invention employing known methods, for example as described in EP application 355,008, published Feb. 21, 1990, or by routine adaptation of such methods.

EXAMPLE 2

Exemplary coupling of LC core to 2-fluoro-2-methyl alkoxy tail 2-(4'-Octyloxyphenyl)-5-[(2S-fluoro-2-methylheptoxy]-pyrimidine Dimethylformamide (5 ml) was added to a mixture of 2-(4'-octyloxyphenyl)-5-hydroxypyrimidine (245 mg), 2S-fluoro-2methylheptyl-1-tosylate (2), (468 ml, 2 eq.), and cesium carbonate (532 mg, 2 eq.) in a dry flask. The solution was stirred for 18 hr at 120° C., poured into aqueous hydrochloric acid (1M, 15 ml) and extracted three times with a 1:1 mixture of ethyl acetate and hexane. The combined organic extracts were washed with brine and dried over sodium sulfate and potassium carbonate. Solvent was removed in vacuo and the residue purified by flash chromatography using a 1:4 ethyl acetate:hexane as the eluent to give 242 mg (77%) of desired product. The product was recrystallized from acetonitrile to give a white solid. This method can be readily adapted for the synthesis of compounds having $R_F$—X tails as indicated in Scheme 2.

The chiral nonracemic 2-fluoro-2-methyl alkoxy tail can be coupled with appropriate LC core precursors by methods exemplified herein, by methods well-known in the art or by routine adaptation of such methods.

EXAMPLE 3

Comparison of Properties of Exemplary chiral nonracemic 2-fluoro-2-methylalkoxy compounds with non-fluorinated and fluorinated achiral tails Table 9 provides an exemplary list of chiral non-racemic 2-fluoro-2-methyl alkoxy compounds having partially fluorinated alkyl or alkoxy tails with mesomorphic properties given. Table 10 is a similar listing of exemplary 2-fluoro-2-methyl ester compounds. Temperatures listed in Table 9 and 10 are in degrees Centigrade. The compounds listed have the S configuration in the chiral tail. Enantiomers of the compounds of Table 9 and 10, having the R configuration in the chiral tail will have mesomorphic properties substantially identical to their corresponding S enantiomer. Signs of pitch and polarization will be reversed between enantiomers.

Table 11 provides a list of 2-fluoro-2-methyl alkoxy and ester compounds which have non-fluorinated alkyl and alkoxy tails for comparison to the compounds of Tables 9 and 10.

EXAMPLE 4

LC mixtures comprising chiral nonracemic 2-fluoro-2-methyl alkoxy compounds

Table 12 provides A-C* transition temperatures and polarization $P_S$ for 10% (w/w) mixtures of exemplary chiral nonracemic compounds with partially fluorinated achiral tails of this invention with liquid crystal host MX6111. Table 13 provides similar data for non-fluorinated tail analogs in 10% (w/w) mixtures of with MX6111. The composition of MX6111 is given in Table 14.

As shown by a comparison of Tables 12 and 13, compounds with partially fluorinated tails ($R_F$—X—) shown enhanced polarization density compared to their non-fluorinated analogs. Higher polarization density FLC compositions generally have faster switching speeds. Compositions containing partially fluorinated tail compounds also display A-C* transitions higher in temperature compared to the non-fluorinated analogs.

Polarization densities (P) are given in $nC/cm^2$ and the magnitude of P was measured by standard techniques by integration of the dynamic current response on reversing the applied electric field, as described in Martinat-Lagarde (1976) *J. Phys.* 37, C-3, p.129 and Martinat-Lagarde (1977) *J. Phys. Lett.* 38, L-17. Tilt angle was measured by standard techniques.

TABLE 1

| EXEMPLARY CORES | |
|---|---|
| $R_1$—X—$Ph_1$—$Ph_2$—R* | Ia |
| $R_1$—X—$Ph_2$—$Ph_1$—R* | Ia' |

| Structure | Label |
|---|---|
| pyrimidine-phenyl core | Ia1/Ia'1 |
| pyrimidine-phenyl core (isomer) | Ia2/Ia'2 |
| pyridine-phenyl core | Ia3/Ia'3 |
| pyridine-phenyl core (isomer) | Ia4/Ia'4 |
| pyrimidine-phenyl core | Ia5/Ia'5 |
| N=N azo-phenyl core | Ia6/Ia'6 |
| phenyl-pyrimidine core | Ia7/Ia'7 |
| difluorophenyl-pyrimidine core | Ia8/Ia'8 |
| difluorophenyl-pyrimidine core | Ia9/Ia'9 |
| difluorophenyl-pyrimidine core | Ia10/Ia'10 |

TABLE 1-continued

EXEMPLARY CORES

| | | |
|---|---|---|
| $R_1-X-Ph_1-Ph_2-R^*$ | Ia | |
| $R_1-X-Ph_2-Ph_1-R^*$ | Ia' | |

| Structure | Label |
|---|---|
| 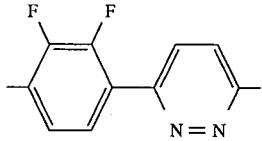 | Ia11/Ia'11 |
| 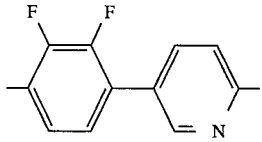 | Ia12/Ia'12 |
| 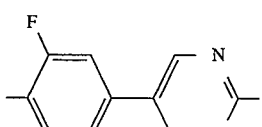 | Ia13/Ia'13 |
| 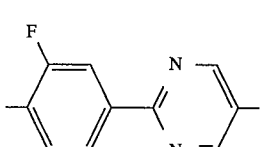 | Ia14/Ia'14 |
| 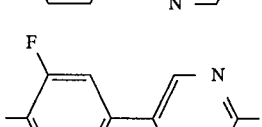 | Ia15/Ia'15 |
| 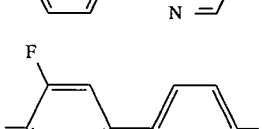 | Ia16/Ia'16 |
| 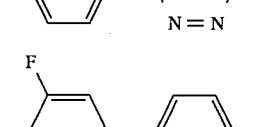 | Ia17/Ia'17 |
| 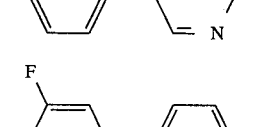 | Ia18/Ia'18 |
| 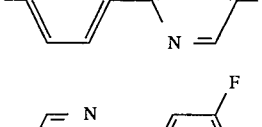 | Ia19/Ia'19 |
| 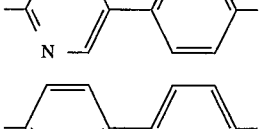 | Ia20/Ia'20 |

TABLE 1-continued

EXEMPLARY CORES

| | | |
|---|---|---|
| $R_1-X-Ph_1-Ph_2-R^*$ | Ia | |
| $R_1-X-Ph_2-Ph_1-R^*$ | Ia' | |

| Structure | Label |
|---|---|
| 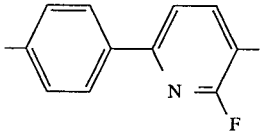 | Ia21/Ia'21 |
| 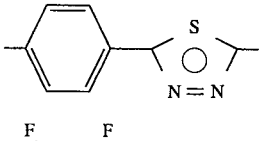 | Ia22/Ia'22 |
| 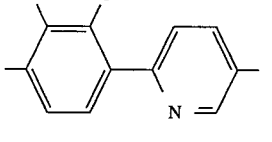 | Ia23/Ia'23 |
| 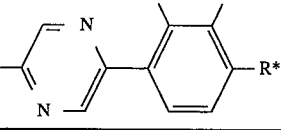 | Ia24/Ia'24 |

TABLE 2

EXEMPLARY CORES

| | | |
|---|---|---|
| $R_1-X-PH_1-B-Ph_2-R^*$ | Ib | |
| $R_1-X-PH_2-B-Ph_1-R^*$ | Ib' | |

| Structure | Label |
|---|---|
| 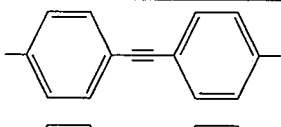 | Ib1 |
| 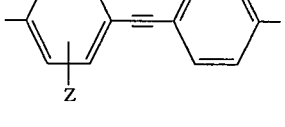 | Ib2/Ib'2 |
| 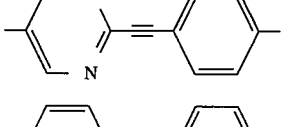 | Ib3/Ib'3 |
| 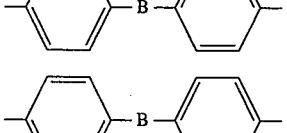 | Ib4/Ib'4 |
| 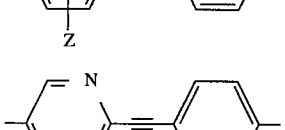 | Ib5/Ib'5 |
| 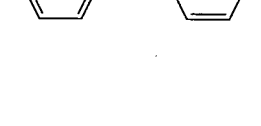 | Ib6/Ib'6 |

TABLE 2-continued

EXEMPLARY CORES

| $R_1-X-PH_1-B-Ph_2-R*$ | Ib |
| $R_1-X-PH_2-B-Ph_1-R*$ | Ib' |

[Structure] Ib7/Ib'7

[Structure] Ib8/Ib'8

[Structure] Ib9/Ib'9

[Structure] Ib10/Ib'10

B is COO or OOC and Z represents either an ortho or meta halogen or both; preferred halogens are fluorines.

TABLE 3

EXEMPLARY CORES

| $R_1-X-Ph_1-Ph_2-Ph_3-R*$ | Ic |
| $R_1-X-Ph_3Ph_2Ph_1-R*$ | Ic' |

[Structure] Ic1

[Structure] Ic2/Ic'2

[Structure] Ic3/Ic'3

[Structure] Ic3/Ib'4

[Structure] Ic5/Ic'5

TABLE 3-continued

EXEMPLARY CORES

| $R_1-X-Ph_1-Ph_2-Ph_3-R*$ | Ic |
| $R_1-X-Ph_3Ph_2Ph_1-R*$ | Ic' |

[Structure] Ic6/Ic'6

[Structure] Ic7/Ic'7

[Structure] Ic8/Ic'8

[Structure] Ic9/Ic'9

[Structure] Ic10/Ic'10

[Structure] Ic11/Ic'11

[Structure] Ic12/Ic'12

[Structure] Ic13/Ic'13

[Structure] Ic14/Ic'14

[Structure] Ic15/Ic'15

TABLE 3-continued

EXEMPLARY CORES

| $R_1-X-Ph_1-Ph_2-Ph_3-R^*$ | Ic |
| $R_1-X-Ph_3Ph_2Ph_1-R^*$ | Ic' |

| Structure | Label |
|---|---|
| [biphenyl-pyridine] | Ic16/Ic'16 |
| [biphenyl(Z)-pyridine] | Ic17/Ic'17 |
| [phenyl-phenyl(Z)-pyridine] | Ic18/Ic'18 |
| [F-phenyl-pyrimidine-phenyl] | Ic19/Ic'19 |
| [phenyl-pyrimidine-F,F-phenyl] | Ic20/Ic'20 |
| [F,F-phenyl-pyrimidine-phenyl] | Ic21/Ic'21 |

Z represents an ortho or meta halogen or both; preferred halogens are fluorines.

TABLE 4

EXEMPLARY CORES OF FORMULAS Id and Ie

| Structure | Label |
|---|---|
| —Ph—CO₂—Ph—Ph— | Id1/Ie1 |
| —Ph(Z)—CO₂—Ph—Ph— | Id2/Ie2 |
| —Ph—CO₂—Ph(Z)—Ph— | Id3/Ie3 |
| —Ph—CO₂—Ph—Ph(Z)— | Id4/Ie4 |
| —Ph—OCO—Ph—Ph— | Id5/Ie5 |
| —Ph—OCO—Ph(Z)—Ph— | Id6/Ie6 |
| —Ph—OCO—Ph—Ph(Z)— | Id7/Ie7 |
| —Ph—OCO—Ph—Ph(Z)— | Id8/Ie8 |
| —Ph—C≡C—Ph—Ph— | Id9/Ie9 |
| —Ph(Z)—C≡C—Ph—Ph— | Id10/Ie10 |
| —Ph—C≡C—Ph(Z)—Ph— | Id11/Ie11 |
| —Ph—C≡C—Ph—Ph(Z)— | Id12/Ie12 |
| —Ph—C≡C—pyrimidine—Ph— | Id13/Ie13 |
| —Ph—C≡C—pyrimidine—Ph(Z)— | Id14/Ie14 |

TABLE 4-continued
EXEMPLARY CORES OF FORMULAS Id and Ie

[Structures Id15/Ie15 through Id34/Ie34 shown]

Z represents ortho or meta halogen substitution or both on the indicated ring; preferred haolgens are fluorine. COres of formula Id are reversed from those of formula Ie with respect to substitutents $R_1$—X and R*;

$Id = R_1$—X—Core—R*

$Ie = R_1$—X—Core—R* for Cores listed above.

TABLE 5

EXEMPLARY CORES OF FORMULA If

R₁—X—Ph₁—B—Ph₂—C—Ph₃—R*

| Structure | If |
|---|---|
| 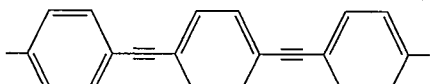 | If1/If1 |
| 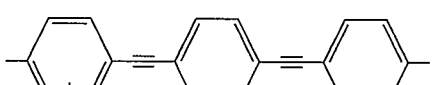 | If2/If2 |
|  | If3/If3 |
| 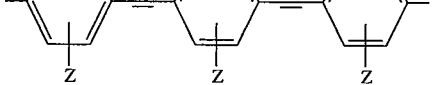 | If4/If4 |
|  | If5/If5 |
| 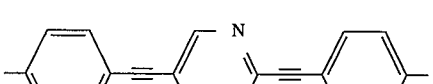 | If6/If6 |
| 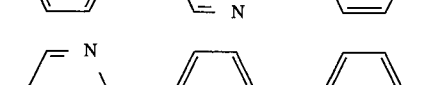 | If7/If7 |
| 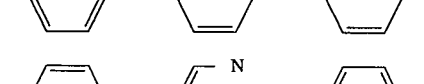 | If8/If8 |
| 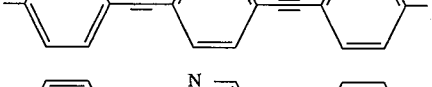 | If9/If9 |
| 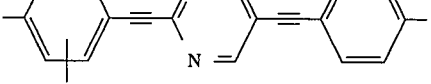 | If10/If10 |
| 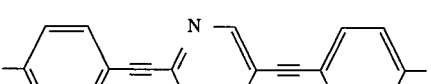 | If11/If11 |
|  | If12/If12 |

TABLE 5-continued

EXEMPLARY CORES OF FORMULA If

R₁—X—Ph₁—B—Ph₂—C—Ph₃—R*

| Structure | If |
|---|---|
| 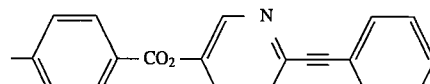 | If13/If13 |
| 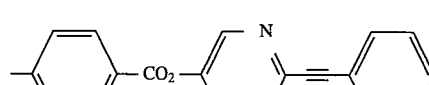 | If14/If14 |
|  | If15/If15 |

TABLE 6

Exemplary Cores of Formula Ig and Ih

| Structure | |
|---|---|
| 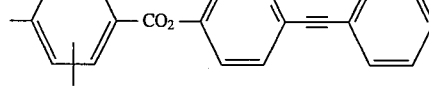 | A = CH₂O Ig<br>A = CH₂CH₂ Ih |
| 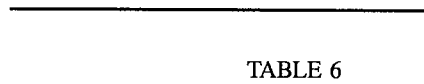 | Ig2/Ih2 |
| 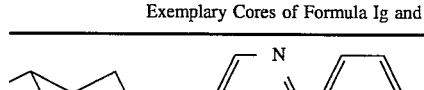 | Ig3/Ih3 |
| 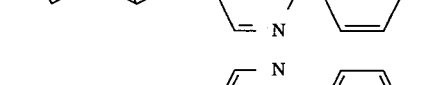 | Ig4/Ih4 |
| 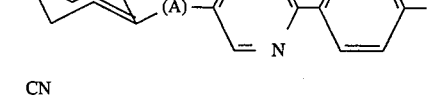 | Ig5/Ih5 |
| 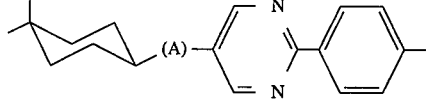 | Ig6/Ih6 |
| 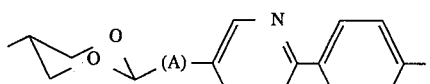 | Ig7/Ih7 |
| 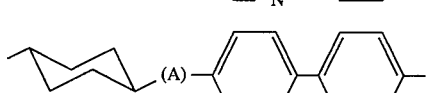 | Ig8/Ih8 |

TABLE 6-continued

Exemplary Cores of Formula Ig and Ih

Ig9/Ih9

Ig10/Ih10

TABLE 7

| Exemplary $R_F$—X— | |
|---|---|
| $R_F$— | $R_F$—O— |
| $CH_3$—$(CH_2)_n$—$CF_2$—$(CH_2)_m$—<br>where: $n + m \leq$ about 18 or<br>$n + 1 = m$ and $n + m \leq$ about 18 | $CH_3$—$(CH_2)_n$—$CF_2$—$(CH_2)_m$—O— |
| $CH_3$—$(CH_2)_n$—$(CF_2)_m$—<br>where: $n + m \leq$ about 19<br>$n + 1 = m$ and $n + m \leq$ about 19 | $CH_3$—$(CH_2)_n$—$(CF_2)_m$—O— |
| $CF_3$—$(CH_2)_n$—<br>where: $n \leq$ about 19 | $CF_3$—$(CH_2)_n$—O— |
| $CF_3CF_2$—$(CH_2)_n$—<br>where: $n \leq$ about 18 | $CF_3CF_2$—$(CH_2)_n$—O— |
| $CF_3$—$(CF_2)_n$—$(CH_2)_m$—<br>where: $n + m \leq$ about 19 or<br>$n + 1 = m$ and $n + m \leq$ about 19 | $CF_3$—$(CF_2)_n$—$(CH_2)_m$—O— |
| $CH_2$=$CH$—$(CF_2)_n$—<br>where: $n \leq$ about 18 | $CH_2$=$CH$—$(CF_2)_n$—O— |
| $CF_2$=$CF$—$(CF_2)_n$—<br>where: $n \leq$ about 18 | $CF_2$=$CF$—$(CF_2)_n$—O— |
| $CF_3$—$(CF_2)_n$—$CH$=$CH$—$(CH_2)_m$—<br>where: $n + m \leq$ about 17 or<br>$n + 1 = m$ and $n + m \leq$ about 17 | $CF_3$—$(CF_2)_n$—$CH$=$CH$—$(CH_2)_m$—O— |
| $CF_3$—$(CF_2)_n$—$(CH_2)_m$—$CH$=$CH$—<br>where: $n + m \leq$ about 17 or<br>$n + 2 = m$ and $n + m \leq$ about 17 | |
| c-propyl-$(CF_2)_n$—<br>where: $n \leq$ about 17 | c-propyl-$(CF_2)_n$—O— |
| $CF_3$—$(CF_2)_n$—<br>where: $n \leq$ about 19 | $CF_3$—$(CF_2)_n$—O— |
| $CF_2H$—$(CF_2)_n$—<br>where: $n \leq$ about 19 | $CF_2H$—$(CF_2)_n$—O— |
| $CF_2H$—$(CF_2)_n$—$(CH_2)_m$—<br>where: $n + m \leq$ about 19 or<br>$n + 1 = m$ and $n + m \leq$ about 19 | $CF_2H$—$(CF_2)_n$—$(CH_2)_m$—O— |

Note: n and m are both integers

TABLE 8

Exemplary $R_2$ $CH_3$—$(CH_3)_n$—
Branched alkyl-
$CH_3$—$Si(CH_3)_2$—$(CH_2)_n$—
$CH_3$—$(CH_3)_n$—$CH$=$CH$—$(CH_2)_m$—
$CH_2$=$CH_2$—$(CH_2)_n$—
$CH_3$—$(CH_2)_n$—$C$≡$C$—$(CH_2)_m$—
$CH_3$—$(CH_2)_n$—$O$—$(CH_2)_m$—
$CH_3$—$(CH_2)_n$—$S$—$(CH_2)_m$—
$CH_3$—$(CH_2)_n$—$CF2$—$(CH_2)_m$—
$CF_3$—$(CH_2)_n$—
$CF_3CF_2$—$(CH_2)_n$ TABLE 8-continued Exemplary $R_2$ $CF_3$—$(CF_2)_n$—$(CH_2)_m$—
$CH_3$—$(CF_2)_n$—$(CH_2)_m$—
$CF_3$—$(CF_2)_n$—
c-cyclopropyl-$(CH_2)_n$—
c-hexyl-$(CH_2)_n$— where: n and m are integers; $n + m <$ about 20.

TABLE 9

| Compound | Structure | Phase Transitions |
|---|---|---|
| MDW987 | C₄F₉C₄H₈O–[pyrimidine]–[phenyl]–O–CH₂–C(CH₃)(F)–C₅H₁₁ | I ↔63↔ A ↔54↔ C ↔21↔ X•, C ↔57↔ Sx ↔53↔ X |
| MDW989 | C₄F₉C₅H₁₀O–[pyrimidine]–[phenyl]–O–CH₂–C(CH₃)(F)–C₅H₁₁ | I ↔69↔ A ↔60↔ C →45→ X ←48← |
| MDW990 | C₆F₁₃C₄H₈O–[pyrimidine]–[phenyl]–O–CH₂–C(CH₃)(F)–C₅H₁₁ | I ↔93↔ A ↔74↔ C ↔65↔ X, A ↔76↔ Sx ↔74↔ X |
| MDW993 | C₄F₉C₅H₁₀O–[phenyl]–[pyrimidine]–O–CH₂–C(CH₃)(F)–C₅H₁₁ | I →54→ X ←61← |
| MDW995 | C₄F₉C₄H₈O–[phenyl]–[pyrimidine]–O–CH₂–C(CH₃)(F)–C₅H₁₁ | I →75→ X ←81← |
| MDW1022 | C₄F₉C₃H₆O–[phenyl]–[pyrimidine]–O–CH₂–C(CH₃)(F)–C₅H₁₁ | I →73→ X ←83← |
| MDW1023 | C₄F₉C₃H₆O–[pyrimidine]–[phenyl]–O–CH₂–C(CH₃)(F)–C₅H₁₁ | I →68→ C →61→ Sx → X ←62← |
| MDW1030 | C₄F₉C₄H₈–[pyrimidine]–[phenyl]–O–CH₂–C(CH₃)(F)–C₅H₁₁ | I →47→ X ←77← | partially fluorinated tail methyl fluoro ethers

TABLE 10

| Compound | Structure | Phase Transitions |
|---|---|---|
| MDW988 | C₄F₉C₄H₈O–[pyrimidine]–[phenyl]–O–C(=O)–C(CH₃)(F)–C₄H₉ | I ↔63↔ A ↔54↔ C ↔21↔ X, C ↔57↔ Sx ↔53↔ X |
| MDW991 | C₆F₁₃C₄H₈O–[pyrimidine]–[phenyl]–O–C(=O)–C(CH₃)(F)–C₄H₉ | I ↔69↔ A ↔60↔ C →45→ X ←48← |
| MDW992 | C₄F₉C₅H₁₀O–[pyrimidine]–[phenyl]–O–C(=O)–C(CH₃)(F)–C₄H₉ | I ↔93↔ A ↔74↔ C ↔65↔ X, A ↔76↔ Sx ↔74↔ X |

TABLE 10-continued

| | | |
|---|---|---|
| MDW994 | $C_6F_{13}C_6H_{12}O$—[pyrimidine]—[phenyl]—O—C(=O)—C(CH$_3$)(F)—C$_4$H$_9$ | I $\xrightarrow{54}$ X $\xleftarrow{61}$ |
| MDW1000 | $C_4F_9C_4H_8O$—[phenyl]—[pyrimidine]—O—C(=O)—C(CH$_3$)(F)—C$_4$H$_9$ | I $\xrightarrow{75}$ X $\xleftarrow{81}$ |
| MDW1020 | $C_4F_9C_3H_6O$—[phenyl]—[pyrimidine]—O—C(=O)—C(CH$_3$)(F)—C$_4$H$_9$ | I $\xrightarrow{78}$ X $\xleftarrow{91}$ |
| MDW1021 | $C_4F_9C_3H_6O$—[pyrimidine]—[phenyl]—O—C(=O)—C(CH$_3$)(F)—C$_4$H$_9$ | I $\xrightarrow{63}$ X $\xleftarrow{75}$ |
| MDW1029 | $C_4F_9C_4H_8$—[pyrimidine]—[phenyl]—O—C(=O)—C(CH$_3$)(F)—C$_4$H$_9$ | I $\xrightarrow{61}$ X $\xleftarrow{69}$ | partially fluorinated tail methyl fluoro esters

TABLE 11

| | | |
|---|---|---|
| MDW746 | $C_{10}H_{21}O$—[phenyl]—[pyrimidine]—O—CH$_2$—C(CH$_3$)(F)—C$_5$H$_{11}$ | I $\xrightarrow{71}$ X $\xleftarrow{93}$ |
| MDW747 | $C_8H_{17}O$—[pyrimidine]—[phenyl]—O—CH$_2$—C(CH$_3$)(F)—C$_5$H$_{11}$ | I $\xleftarrow{130}$ A $\xleftarrow{126}$ C $\xrightarrow{89}$ Sx $\xrightarrow{87}$ X |
| MDW1005 | $C_{10}H_{21}$—[phenyl]—CO$_2$—[phenyl]—O—CH$_2$—C(CH$_3$)(F)—C$_5$H$_{11}$ | I $\xrightarrow{22}$ X $\xleftarrow{33}$ |
| MDW1006 | $C_{10}H_{21}O$—[phenyl]—CO$_2$—[phenyl]—O—CH$_2$—C(CH$_3$)(F)—C$_5$H$_{11}$ | I $\xrightarrow{41}$ X $\xleftarrow{53}$ |
| MDW581 | $C_8H_{17}O$—[pyrimidine]—[phenyl]—O—C(=O)—C(CH$_3$)(F)—C$_5$H$_{11}$ | I $\xrightarrow{49}$ X $\xleftarrow{68}$ |
| MDW582 | $C_{10}H_{21}O$—[pyrimidine]—[phenyl]—O—C(=O)—C(CH$_3$)(F)—C$_5$H$_{11}$ | I $\xrightarrow{37}$ A $\xrightarrow{34}$ X $\xleftarrow{43}$ |

Examples of two-ring 2-methyl-2S-fluoro ether and ester dopants

TABLE 12

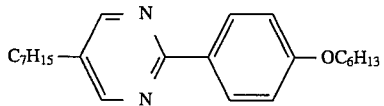

Partially fluorinated two-ring methyl fluoro ethers - enhancement in A–C* and $P_s$

| Compound | A–C* transition in MX6111 | $P_s$ in 10% in MX6111 |
|---|---|---|
| MDW987 | 64 | 4.1 |
| MDW989 | 64 | 2.4 |
| MDW990 | 67 | 3.8 |
| MDW993 | 56 | 4.5 |
| MDW995 | 57 | 5.7 |
| MDW1030 | 58 | 5.7 |
| MDW988 | 65 | 7.6 |
| MDW991 | — | 5.8 |
| MDW992 | 69 | 6.9 |
| MDW994 | 65 | 3.4 |
| MDW1000 | 62 | 7.2 |
| MDW1029 | 57 | 10.2 |

R* = methyl fluoroether or ester
X = O or single bond (for compounds below)

TABLE 13

Phase suppression and very low polarization of non tail-fluorinated two-ring methylfluoro dopants

| Compound | A–C* transition in MX6111[1] | $P_s$ in 10% in MX6111 |
|---|---|---|
| MDW746 | 32 | <0.2 |
| MDW747 | 22 | <0.2 |
| MDW1005 | 20 | <0.2 |
| MDW1006 | 31 | <0.2 |
| MDW581 | 57 | 0.6 |
| MDW582 | 53 | <0.2 |

[1]In °C., for MX6111 A–C* is 57° C.

TABLE 14

The composition of MX6111 is:

| Short name MX6111 (% w/w) | Structure | |
|---|---|---|
| 706 | 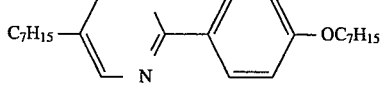 | 5.6 |
| 707 | 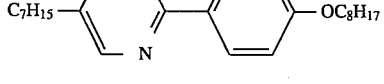 | 5.6 |
| 708 | 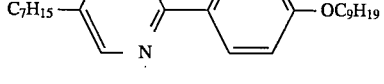 | 5.6 |
| 709 | 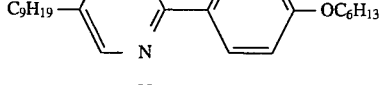 | 7.2 |
| 906 | 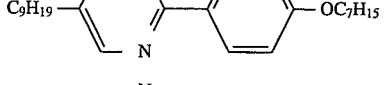 | 9.6 |
| 907 | 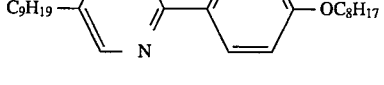 | 7.2 |
| 908 | 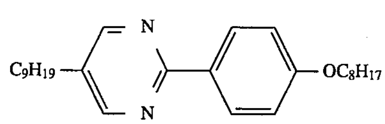 | 5.6 |

TABLE 14-continued
The composition of MX6111 is:
| Short name MX6111 (% w/w) | Structure | |
|---|---|---|
| 909 | $C_9H_{19}$—[pyrimidine]—[phenyl]—$OC_9H_{19}$ | 33.6 |
| 900H | $C_9H_{19}$—[pyrimidine]—[phenyl]—O—CH$_2$—[cyclohexyl]—CH=CH—CH$_2$—CH=CH—CH$_3$ | 20 |
Scheme 1
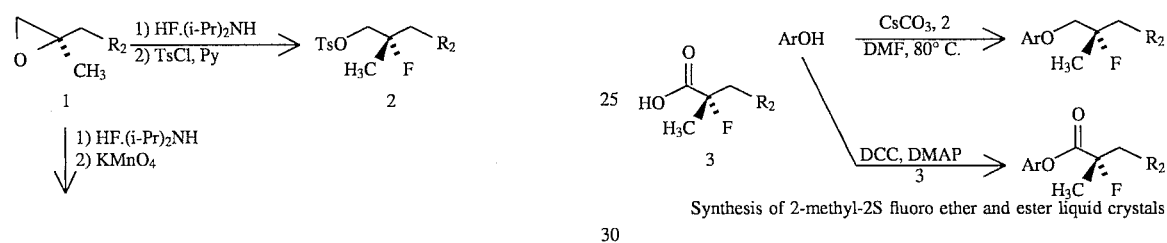
Synthesis of 2-methyl-2S fluoro ether and ester liquid crystals
Scheme 2
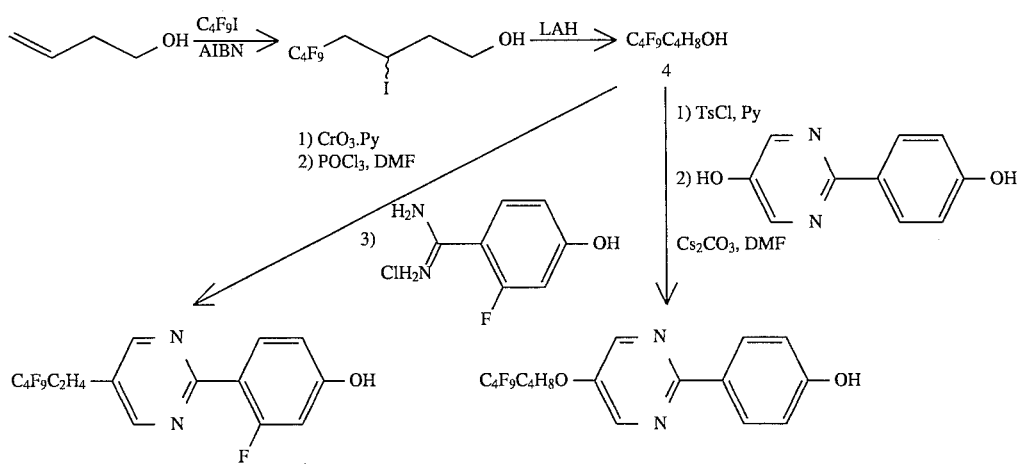
Synthesis of partially fluorinated tail alkyl and alkoxyphenylpyrimidines -continued
Scheme 2

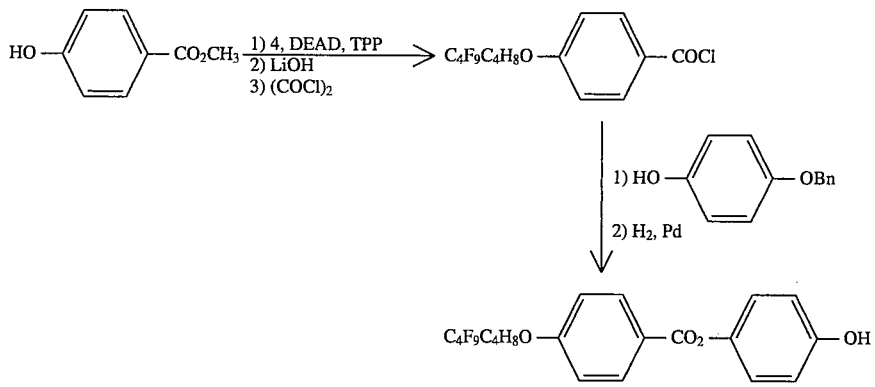

Synthesis of partially fluorinated tail phenylbenzoates

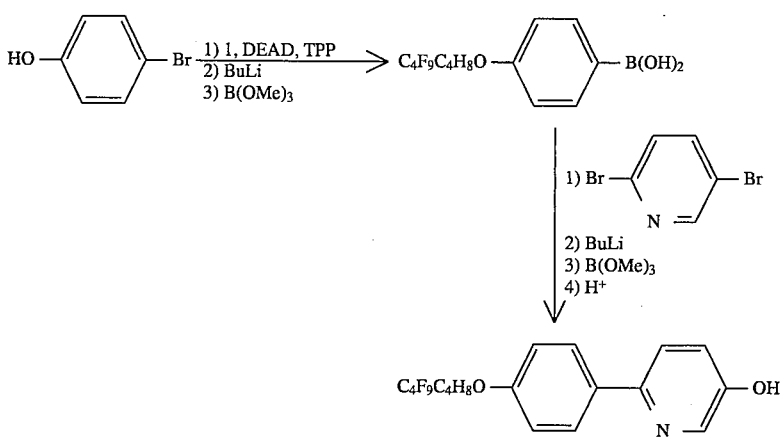

Synthesis of partially fluorinated tail phenylpyridines

We claim:
1. A chiral nonracemic composed of formula:

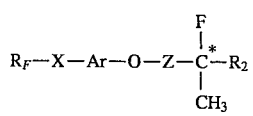

wherein Z is a C=O group or a $CH_2$ group; $R_F$ is a partially or fully fluorinated alkyl or alkenyl group having from one to about twenty carbon atoms; $R_2$ is selected from the group consisting of an alkyl, alkenyl or alkynyl group having from two to about twenty carbon atoms in which one or more $CH_2$ groups may optionally be substituted with one or two halogen atoms or in which one or more non-neighboring $CH_2$ groups may be replaced with an O, S or an alkyl silyl group, $Si(R_A)(R_B)$, in which $R_A$ and $R_B$, independently of one another, are small alkyl or alkenyl groups having from one to six carbon atoms; * indicates the chiral carbon; and Ar is a one, two, or three aromatic ring LC core moiety of the general formula:

$$-(Cyc)_n-(A)_a-Ph_1-(B)_b-(Ph_2)_m-(C)_c-(Ph_3)_p-$$

where n, m and p, independently of one another, are 0 or 1; a, b and c are either 0 or 1 and a+b+c is 2, 1 or 0; A, B and C, independently of one another, are selected from the group consisting of O, S, $CH_2S$, $SCH_2$, $CH_2CH_2$, $CH_2O$, $OCH_2$, $CH_2CO$, $CH_2OCO$, COO, OOC, COS, a —C≡C—; or —C≡C— group; Cyc is a 1,4-cyclohexyl ring or a 1,4-cyclohexenyl ring, either of which may be further substituted with halogen atoms or cyano groups and wherein one or two non-neighboring $CH_2$ groups of the ring may be replaced with an O atom; and the aromatic rings $Ph_1$, $Ph_2$ and $Ph_3$, independently of one another, are selected from the group 1,4-phenyl, 1,4-phenyl substituted with one or two halogen atoms, 1,4-phenyl in which one or two of the ring carbons are replaced with nitrogen atoms or a thiadiazole ring; X is an O or a single bond wherein when n=0, a is also 0, when m=0, b is also 0 and when p=0, c is also 0.

2. A chiral nonracemic compound of claim 1 wherein Z is a $CH_2$ group.

3. A chiral nonracemic compound of claim 2 having a core with one or two aromatic rings wherein Ar is:

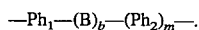

4. The compound of claim 3 wherein $Ph_1$ and $Ph_2$, independently of one another, are selected from the group consisting of 1,4-phenyl, 1,4-phenyl substituted with 1 or 2 fluorine atoms, a 2,5-pyrimidinyl or a 2,5-pyridinyl group.

5. The compound of claim 3 wherein at least one of $Ph_1$ or $Ph_2$ is a 2,5-pyrimidinyl or a 2,5-pyridinyl group.

6. The compound of claim 3 wherein at least the core is a phenyl benzoate or a reverse phenyl benzoate.

7. A chiral nonracemic compound of claim 2 having a core with one aromatic ring wherein Ar is —$Ph_1$—.

8. The compound of claim 7 wherein Ph$_1$ is selected from the group consisting of 1,4-phenyl, 1,4-phenyl substituted with 1 or 2 fluorine atoms, a 2,5-pyrimidinyl or a 2,5-pyridinyl group.

9. A chiral nonracemic compound of claim 1 wherein Z is C=O.

10. A chiral nonracemic compound of claim 9 having a core with one or two aromatic rings wherein Ar is:

—Ph$_1$—(B)$_b$—(Ph$_2$)$_m$—.

11. The compound of claim 10 wherein Ph$_1$ and Ph$_2$, independently of one another, are selected from the group consisting of 1,4-phenyl, 1,4-phenyl substituted with 1 or 2 fluorine atoms, a 2,5-pyrimidinyl or a 2,5-pyridinyl group.

12. The chiral nonracemic compound of claim 9 having a core with one aromatic ring wherein Ar is —Ph$_1$—.

13. The compound of claim 12 wherein Ph$_1$ is selected from the group consisting of 1,4-phenyl, 1,4-phenyl substituted with 1 or 2 fluorine atoms, a 2,5-pyrimidinyl or a 2,5-pyridinyl group.

14. The compound of claim 1 wherein at least one of Ph$_1$, Ph$_2$ and Ph$_3$ is a pyrimidinyl or a 2,5-pyridinyl group.

15. The compound of claim 1 wherein R$_F$—X— is a partially fluorinated alkyl group.

16. The compound of claim 1 wherein R$_F$—X— is a fully fluorinated alkyl group.

17. The compound of claim 1 wherein R$_F$—X— is a partially fluorinated alkoxy group.

18. An FLC composition which comprises one or more of the chiral nonracemic compounds of claim 1.

19. An FLC composition which comprises one or more of the chiral nonracemic compounds of claim 2.

20. An FLC composition which comprises one or more of the chiral nonracemic compounds of claim 9.

21. The compound of claim 1 wherein Ar is:

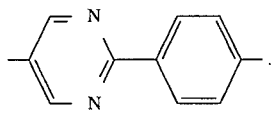

22. The compound of claim 1 wherein Ar is:

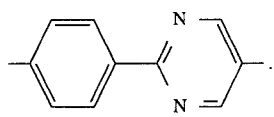

* * * * *

UNITED STATES PATENT AND TRADEMARK OFFICE
CERTIFICATE OF CORRECTION

PATENT NO. : 5,585,036

DATED : Dec. 17, 1996

INVENTOR(S) : Wand et al.

It is certified that error appears in the above-identified patent and that said Letters Patent is hereby corrected as shown below:

At column 1, lines 7-12, "This application is a continuation-in-part of Ser. No. 193,254, now U.S. Pat. No. 5,455,218, filed Feb. 8, 1994 which in turn was a continuation-in-part of Ser. No. 006,263, now U.S. Pat. No. 5,422,037, filed Jan. 19, 1993, which in turn is a continuation-in-part of Ser. No. 164,235, filed Mar. 4, 1988, now U.S. Pat. No. 5,051,506, issued Sep. 29, 1991." should read --This application is a continuation-in-part of co-pending U.S. Pat. No. 5,453,218, filed Feb. 8, 1994, which in turn was a continuation-in-part of U.S. Pat. 5,422,037, filed Jan. 19, 1993, which in turn is a continuation-in-part of U.S. Pat. No. 5,051,506, issued Sep. 29, 1991.--.

At column 12, line 12, "each and" should read --each other and--.

At column 16, at the 2nd exemplary core of TABLE 1-continued (Ia22/Ia'22),

At column 17, TABLE 3, 4th exemplary cores "Ic3/Ib'4" should read --Ic4/Ic'4--.

At column 22, next-to-last line of the column, "Id=$R_1$—X—Core—R*" should read --Id = $R_1$—X—Core—R*--.

UNITED STATES PATENT AND TRADEMARK OFFICE
CERTIFICATE OF CORRECTION

PATENT NO. : 5,585,036

DATED : Dec. 17, 1996

INVENTOR(S) : Wand et al.

It is certified that error appears in the above-identified patent and that said Letters Patent is hereby corrected as shown below:

At column 22, last line of the column, "$Ie=R_1-X-Core-R^*$" should read --$Ic = R_1-X-Core-R^*$--.

At column 25, TABLE 8, first entry of the table, "$CH_3-(CH_3)_n-$" should read --$CH_3-(CH_2)_n-$--.

At column 25, TABLE 8, 4th entry of the table, "$CH_3-(CH_3)_n-CH=CH-(CH_2)_m-$" should read --$CH_3-(CH_2)_n-CH=CH-(CH_2)_m-$--.

At column 26, line 10, "$<$" should read --$\leq$--.

At column 28, TABLE 9, third column, first row, the phase diagram, " 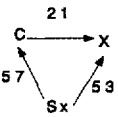 " should read -- 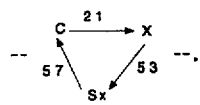 --.

At column 28, TABLE 9, third column, third row, the phase diagram, " 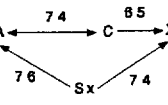 " should read -- 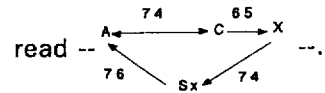 --.

UNITED STATES PATENT AND TRADEMARK OFFICE
CERTIFICATE OF CORRECTION

PATENT NO. : 5,585,036

DATED : Dec. 17, 1996

INVENTOR(S) : Wand et al.

It is certified that error appears in the above-identified patent and that said Letters Patent is hereby corrected as shown below:

At column 28, TABLE 10, third column, first row, the phase diagram, " 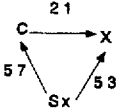 " should read -- 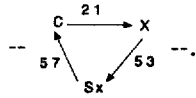 --.

At column 28, TABLE 10, third column, third row, the phase diagram, " 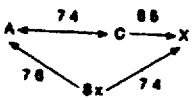 " should read -- 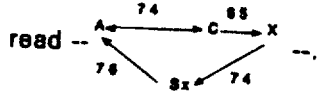 --.

At column 31, Table 12, in the descriptive title of the Table, "fluoro ethers -" should read -- fluoro ethers and esters - --.

At column 31, Table 12, last line of the footnotes to the table, "below)" should read --above)--.

UNITED STATES PATENT AND TRADEMARK OFFICE
CERTIFICATE OF CORRECTION

PATENT NO. : 5,585,036

DATED : Dec. 17, 1996

INVENTOR(S) : Wand et al.

It is certified that error appears in the above-identified patent and that said Letters Patent is hereby corrected as shown below:

At column 35, last line of the column, "$CH_2CO$," should read --$CH_2CO_2$-- and ";" should be deleted.

At column 36, first line of claim 6, please delete "at least".

Signed and Sealed this

Fifth Day of August, 1997

Attest:

Attesting Officer

BRUCE LEHMAN

Commissioner of Patents and Trademarks